United States Patent
Anjur et al.

[11] Patent Number: 5,849,000
[45] Date of Patent: Dec. 15, 1998

[54] ABSORBENT STRUCTURE HAVING IMPROVED LIQUID PERMEABILITY

[75] Inventors: Sriram Padmanabhan Anjur, Appleton; Michael Franklin Kalmon, Brillion; Anthony John Wisneski, Kimberly, all of Wis.

[73] Assignee: Kimberly-Clark Worldwide, Inc., Neenah, Wis.

[21] Appl. No.: 366,199

[22] Filed: Dec. 29, 1994

[51] Int. Cl.⁶ .................................................. A61F 16/16
[52] U.S. Cl. ........................... 604/367; 604/368; 604/370
[58] Field of Search .................................. 604/366–368, 604/385.1, 365, 370, 372, 358, 384; 428/171, 172, 221, 283, 224

[56] References Cited

U.S. PATENT DOCUMENTS

| | | | |
|---|---|---|---|
| 3,811,957 | 5/1974 | Buntin | 136/146 |
| 4,100,324 | 7/1978 | Anderson et al. | 428/288 |
| 4,426,417 | 1/1984 | Meitner et al. | 428/195 |
| 4,429,001 | 1/1984 | Kolpin et al. | 428/283 |
| 4,560,372 | 12/1985 | Pieniak | 604/369 |
| 4,623,576 | 11/1986 | Lloyd et al. | 428/171 |
| 4,650,479 | 3/1987 | Insley | 604/358 |
| 4,655,757 | 4/1987 | McFarland et al. | 604/366 |
| 4,724,114 | 2/1988 | McFarland et al. | 264/510 |
| 4,773,903 | 9/1988 | Weisman et al. | 604/368 |
| 4,834,735 | 5/1989 | Alemany et al. | 604/368 |
| 4,865,596 | 9/1989 | Weisman et al. | 604/368 |
| 4,879,170 | 11/1989 | Radwanski | 428/233 |
| 4,923,454 | 5/1990 | Seymour et al. | 604/368 |
| 4,931,355 | 6/1990 | Radwanski et al. | 428/283 |
| 4,939,016 | 7/1990 | Radwanski et al. | 428/152 |
| 4,950,531 | 8/1990 | Radwanski et al. | 428/284 |
| 4,957,795 | 9/1990 | Riedel | 428/74 |
| 4,988,560 | 1/1991 | Meyer et al. | 428/297 |
| 5,047,023 | 9/1991 | Berg | 604/368 |
| 5,149,335 | 9/1992 | Kellenberger et al. | 604/385.1 |
| 5,246,429 | 9/1993 | Poccia et al. | 604/368 |
| 5,350,370 | 9/1994 | Jackson et al. | 604/367 |
| 5,391,161 | 2/1995 | Hellgren et al. | 604/366 |

FOREIGN PATENT DOCUMENTS

| | | |
|---|---|---|
| 0080382A3 | 6/1983 | European Pat. Off. . |
| 0 156 649 A2 | 10/1985 | European Pat. Off. . |
| 0 159 630 A2 | 10/1985 | European Pat. Off. . |
| 0 174 775 A1 | 3/1986 | European Pat. Off. . |
| 0 210 968 A2 | 2/1987 | European Pat. Off. . |
| 0 294 137 A1 | 12/1988 | European Pat. Off. . |
| 0306262A1 | 3/1989 | European Pat. Off. . |
| 0633009A2 | 1/1995 | European Pat. Off. . |
| 2 214 201 A | 8/1989 | United Kingdom . |
| 2 284 551 A | 6/1995 | United Kingdom . |

*Primary Examiner*—John G. Weiss
*Assistant Examiner*—David J. Cho
*Attorney, Agent, or Firm*—John R. Schenian

[57] ABSTRACT

Disclosed is an absorbent structure containing hydrogel-forming polymeric material, wettable staple fiber, and wettable binder fiber. The absorbent structure exhibits improved z-direction permeability of a liquid as compared to an otherwise essentially identical absorbent structure which does not comprise a wettable binder fiber. Also disclosed is an disposable absorbent product containing such an absorbent structure.

21 Claims, 2 Drawing Sheets

ABSORBENT STRUCTURE HAVING IMPROVED LIQUID PERMEABILITY

BACKGROUND OF THE INVENTION

1. Field of the Invention

The present invention relates to an absorbent structure suitable for use in disposable absorbent products. More particularly, the present invention relates to an absorbent structure, comprising hydrogel-forming polymeric material, wettable staple fiber, and wettable binder fiber, that exhibits improved liquid-handling capabilities.

2. Description of the Related Art

The purpose of disposable absorbent products is typically body waste management. In order to manage liquid body waste, the absorbent structure within an absorbent product must generally be able to first uptake the liquid into the absorbent product, then distribute the liquid within the absorbent product, and then retain the liquid within the absorbent product.

It is generally important that the absorbent structure uptake the liquid at about the rate of delivery of the liquid to the absorbent product or else the liquid may run off the surface of the absorbent structure and not be present for the absorbent structure to distribute and retain the liquid within the absorbent product. That is, if the liquid uptake rate of the absorbent structure is less than the delivery rate of the liquid to the absorbent product, there exists the possibility of leakage of the liquid from the absorbent product.

In addition, if the distribution of the liquid by the absorbent structure within the absorbent product is not adequate, the efficiency of the utilization of the absorbent structure will be low. Typically, commercially available absorbent products are designed with an excess absolute liquid saturated retention capacity. Thus, the absorbent structure in the absorbent product is often not fully utilized. An increase in distribution efficiency of the liquid by the absorbent material would potentially allow for either a higher realized liquid saturation level for an absorbent product using the same amount of absorbent structure or the use of less absorbent structure to achieve the same realized liquid saturation level in the absorbent product without any increase in liquid leakage. The use of less absorbent structure to achieve the same realized liquid saturation level in an absorbent product will typically result in less absorbent product being disposed of to the environment.

Absorbent structures suitable for use in absorbent products are generally well known. Originally, it was a general practice to form absorbent structures comprising an absorbent fibrous matrix entirely from wood pulp fluff, such as a batt of comminuted wood pulp fluff. Given the relatively low amount of liquid absorbed by wood pulp fluff on a gram of liquid absorbed per gram of wood pulp fluff basis, it is necessary to employ relatively large quantities of wood pulp fluff, thus, necessitating the use of relatively large, thick absorbent structures.

In order to enhance the absorbent capacity of such absorbent structures, it is common to incorporate into them a hydrogel-forming polymeric material. Such hydrogel-forming polymeric materials are generally capable of absorbing at least about 10 times their weight in water. The introduction of hydrogel-forming polymeric materials into such absorbent structures allows for the use of less wood pulp fluff, since the hydrogel-forming polymeric material generally has a higher liquid absorption capacity on a gram per gram basis than the wood pulp fluff. Moreover, such hydrogel-forming polymeric materials are generally less pressure sensitive than wood pulp fluff. Thus, the use of the hydrogel-forming polymeric materials generally allows for the production and use of a smaller, thinner absorbent product.

One problem with known absorbent structures comprising hydrogel-forming polymeric material and fibers that are essentially wood pulp fluff fibers is that when wetted with too much liquid, the absorbent structure is likely to collapse, thus inhibiting the flow of the liquid through the absorbent structure. Furthermore, such known absorbent structures generally have a poor integrity when they are wet, thus making the absorbent structure susceptible to breaking apart when wet and making the absorbent structure difficult to handle separately without the use of enclosing materials such as a tissue wrap sheet.

SUMMARY OF THE INVENTION

It is desirable to produce an absorbent structure able to meet or exceed the performance characteristics of known absorbent structures while containing a relatively high concentration of hydrogel-forming polymeric material. It is also desired to produce an absorbent structure which is able to rapidly absorb a discharged liquid under pressures typically encountered during use and to retain the absorbed liquid under pressures typically encountered during use. Further, it is desired to produce an absorbent structure that, when wet, substantially maintains its integrity and substantially maintains or improves its liquid-handling capabilities.

These and other related goals are achieved by an absorbent structure comprising a hydrogel-forming polymeric material, a wettable staple fiber, and a wettable binder fiber, wherein the absorbent structure exhibits improved Z-Direction Permeability values as compared to an otherwise essentially identical absorbent structure which does not comprise a wettable binder fiber.

In one embodiment of the present invention, an absorbent structure comprises from about 20 to about 65 weight percent hydrogel-forming polymeric material, from about 25 to about 70 weight percent wettable staple fiber and from greater than about 7 to about 40 weight percent wettable binder fiber, wherein all weight percents are based on the total weight of the hydrogel-forming polymeric material, wettable staple fiber, and wettable binder fiber in the absorbent structure. The absorbent structure exhibits a Z-Direction Permeability at 60 percent saturation that is not less than the Z-Direction Permeability of the absorbent structure at 30 percent saturation. The absorbent structure also exhibits a Z-Direction Permeability at 60 percent saturation that is greater than about 50 Darcy.

In another aspect, it is desirable to provide a thin disposable absorbent product, such as an infant diaper, which disposable absorbent product employs an absorbent structure having a relatively small volume and a high concentration of hydrogel-forming polymeric material. Further, it is desirable to provide a disposable absorbent product which has a relatively small volume and a relatively high capacity.

In one embodiment, these goals are achieved in a disposable absorbent product comprising a liquid-permeable topsheet, a backsheet, and an absorbent structure of the present invention positioned between the topsheet and the backsheet.

DETAILED DESCRIPTION OF THE PREFERRED EMBODIMENT

Figure 1:
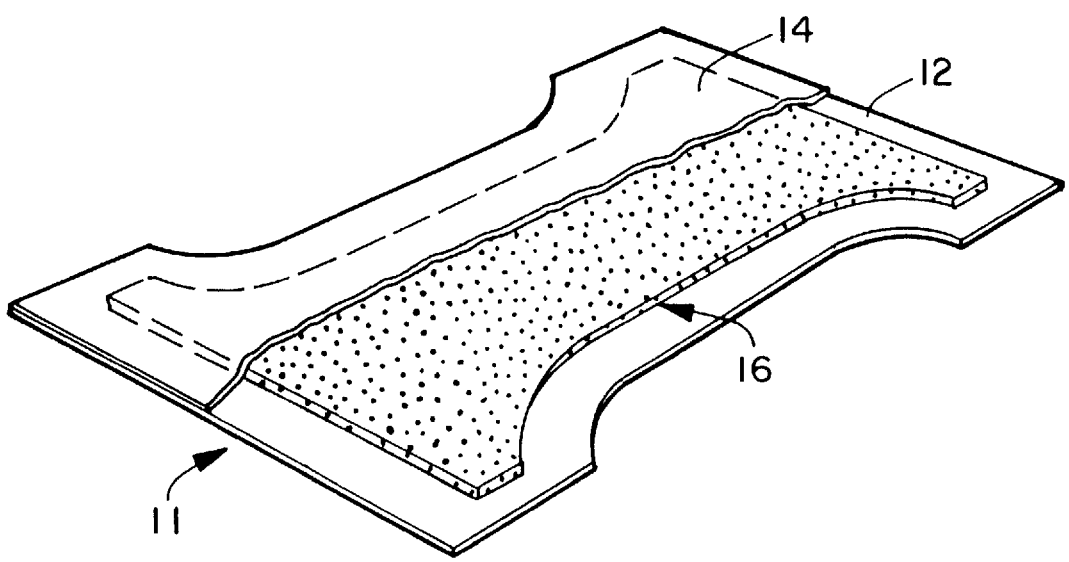
FIG. 1 is a perspective view of one embodiment of a disposable absorbent product according to the present invention.
Figure 2:
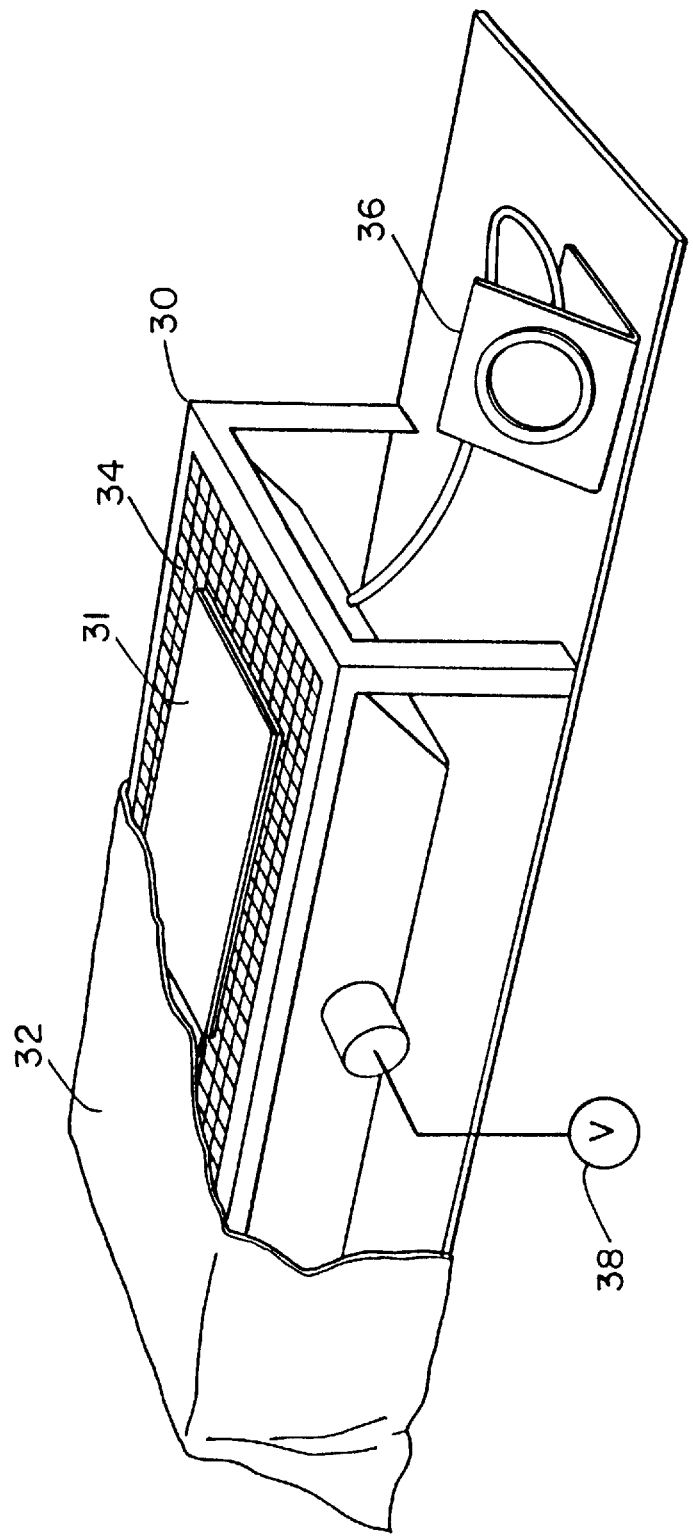
FIG. 2 is an illustration of the equipment employed in determining the liquid saturated retention capacity of an absorbent structure.

In one aspect, the present invention concerns an absorbent structure useful in a disposable absorbent product possessing improved, desirable liquid-handling characteristics achievable by the careful selection and use of hydrogel-forming polymeric material, wettable staple fiber, and wettable binder fiber employed in forming such absorbent structures.

As used herein, "hydrogel-forming polymeric material" is meant to refer to a high absorbency material commonly referred to as a superabsorbent material. Such high absorbency materials are generally capable of absorbing an amount of a liquid, such as synthetic urine, a 0.9 weight percent aqueous saline solution, or bodily fluids, such as menses, urine, or blood, at least about 10, suitably about 20, and up to about 100 times the weight of the hydrogel-forming polymeric material at the conditions under which the hydrogel-forming polymeric material is being used. Typical conditions include, for example, a temperature of between about 0° C. to about 100° C. and suitably ambient conditions, such as about 23° C. and about 30 to about 60 percent relative humidity. Upon absorption of the liquid, the hydrogel-forming polymeric material typically swells and forms a hydrogel.

The hydrogel-forming polymeric material may be formed from an organic hydrogel material which may include natural materials, such as agar, pectin, and guar gum, as well as synthetic materials, such as synthetic hydrogel polymers. Synthetic hydrogel polymers include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyridines. Other suitable hydrogel polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble yet water swellable. Crosslinking may, for example, be by irradiation or covalent, ionic, van der Waals, or hydrogen bonding. Suitable hydrogel-forming polymeric materials are typically available from various commercial vendors, such as The Dow Chemical Company, Hoechst Celanese, Allied Colloids Limited, or Stockhausen, Inc.

The hydrogel-forming polymeric material, employed in the absorbent structures or products of the present invention, suitably should be able to absorb a liquid under an applied load. For the purposes of this application, the ability of a hydrogel-forming polymeric material to absorb a liquid under an applied load, and thereby perform work, is quantified as the Absorbency Under Load (AUL) value. The AUL value is expressed as the amount (in grams) of an aqueous 0.9 weight percent sodium chloride solution which the hydrogel-forming polymeric material can absorb in about 60 minutes per gram of hydrogel-forming polymeric material under a load of about 0.3 pound per square inch (approximately 2.0 kilopascals) while restrained from swelling in the plane normal to the applied load. The hydrogel-forming polymeric material employed in the absorbent structures of the present invention suitably exhibit an AUL value of at least about 15, more suitably of at least about 20, and up to about 50 grams of liquid per gram of hydrogel-forming polymeric material. The method by which the AUL value may be determined is set forth, for example, in detail in U.S. Pat. No. 5,149,335 or U.S. Pat. No. 5,247,072, incorporated herein by reference.

Suitably, the hydrogel-forming polymeric material is in the form of particles which, in the unswollen state, have maximum cross-sectional diameters within the range of from about 50 micrometers to about 1000 micrometers, preferably within the range of from about 100 micrometers to about 800 micrometers, as determined by sieve analysis according to American Society for Testing and Materials (ASTM) test method D-1921. It is to be understood that the particles of hydrogel-forming polymeric material falling within the ranges described above may comprise solid particles, porous particles, or may be agglomerated particles comprising many smaller particles agglomerated into particles falling within the described size ranges.

The hydrogel-forming polymeric material is typically present in an absorbent structure or product of the present invention in an amount effective to result in the absorbent structure or product being able to absorb a desired amount of liquid and in the absorbent structure exhibiting the desired absorbent properties. As such, the hydrogel-forming polymeric material should be present in the absorbent structure in more than a minimal amount so that the absorbent structure exhibits the desired absorbent properties. However, the hydrogel-forming polymeric material should be present in the absorbent structure in less than an excessive amount so that the absorbent structure does not experience gel blocking by the swollen hydrogel-forming polymeric material that may undesirably affect the absorbent properties of the absorbent structure.

The hydrogel-forming polymeric material is therefore desirably present in an absorbent structure of the present invention in an amount of from about 20 to about 65 weight percent, suitably in an amount of from about 25 to about 60 weight percent, and more suitably of from about 30 to about 55 weight percent, based on the total weight of the hydrogel-forming polymeric material, wettable staple fiber, and wettable binder fiber in the absorbent structure. Because the hydrogel-forming polymeric materials present in the absorbent structures of the present invention can be present in high concentrations, the absorbent structures of the present invention can be relatively thin and light weight, have a relatively small volume, and still function in a desirable manner.

As used herein, the term "staple fiber" is meant to refer to a natural fiber or a length cut from, for example, a manufactured filament. Such staple fibers are intended to act in the absorbent structure of the present invention as a temporary reservoir for liquid and also as a conduit for liquid distribution.

Preferably, the staple fibers used in the absorbent structures herein should range in length from about 0.1 to about 15 cm, and suitably from about 0.2 to about 7 cm. Staple fibers of these size characteristics, when combined with the wettable binder fiber and hydrogel-forming polymeric material herein, help to impart desirable bulk, improved liquid acquisition, liquid distribution and strength characteristics, and/or desirable flexibility and resilience properties to the absorbent structures of this invention.

As used herein, the term "wettable" is meant to refer to a fiber which exhibits a liquid, such as water, synthetic urine, or a 0.9 weight percent aqueous saline solution, in air contact angle of less than 90°. As used herein, the contact angle may be determined, for example, as set forth by Robert J. Good and Robert J. Stromberg, Ed., in "Surface and Colloid Science -Experimental Methods", Vol. 11, (Plenum Press, 1979). Suitably, a wettable fiber refers to a fiber which exhibits a synthetic urine in air contact angle of less than 90° at a temperature between about 0° C. and about 100° C. and suitably at ambient conditions, such as about 23° C.

Suitable wettable fibers may be formed from intrinsically wettable fibers or may be formed from intrinsically hydrophobic fibers having a surface treatment thereon which renders the fiber hydrophilic. When surface treated fibers are employed, the surface treatment is desirably nonfugitive. That is, the surface treatment desirably does not wash off the surface of the fiber with the first liquid insult or contact. For the purposes of this application, a surface treatment on a generally hydrophobic polymer will be considered to be nonfugitive when a majority of the fibers demonstrate a liquid in air contact angle of less than 90° for three consecutive contact angle measurements, with drying between each measurement. That is, the same fiber is subjected to three separate contact angle determinations and, if all three of the contact angle determinations indicate a contact angle of liquid in air of less than 90°, the surface treatment on the fiber will be considered to be nonfugitive. If the surface treatment is fugitive, the surface treatment will tend to wash off of the fiber during the first contact angle measurement, thus, exposing the hydrophobic surface of the underlying fiber and will demonstrate subsequent contact angle measurements greater than 90°.

If a surface-treatment is used, the surface treatment is suitably used in an amount of less than about 5 weight percent, more suitably of less than about 3 weight percent, and most suitably of less than about 2 weight percent, based on the amount of fiber being treated.

As used herein, the term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

A wide variety of staple fiber materials can be employed in the absorbent structures herein. Staple fibers useful in the present invention may be formed from natural or synthetic materials and may include cellulosic fibers such as wood pulp fibers and modified cellulose fibers, textile fibers such as cotton or rayon, and substantially nonabsorbent synthetic polymeric fibers.

For reasons of availability and cost, cellulosic fibers will frequently be preferred for use as the staple fiber component of the absorbent structures of this invention. Most preferred are wood pulp fibers. However, other cellulosic fiber materials, such as cotton fibers, may also be used as the staple fiber. The staple fibers used herein may also be crimped in order for the resulting absorbent structure to have the desired resilience and resistance to bunching during use in absorbent products. Crimped staple fibers are those which have a continuous wavy, curvy or jagged character along their length. Fiber crimping of this sort is described more fully in U.S. Pat. No. 4,118,531, incorporated herein by reference.

The wettable staple fibers should be present in the absorbent structure of the present invention in an amount effective to result in the desired improvement in absorbent properties described herein as compared to an otherwise essentially identical absorbent structure that does not comprise any wettable binder fiber.

As such, the wettable staple fibers should be present in the absorbent structure in less than an excessive amount so that the absorbent structure does not experience an undesirable loss of integrity or an undesirable structure collapse when the absorbent structure becomes saturated with a liquid. In addition, the hydrogel-forming polymeric material should be present in the absorbent structure in more than a minimal amount so that the absorbent structure exhibits the desired absorbent properties.

The wettable staple fiber is therefore desirably present in an absorbent structure of the present invention in an amount from about 25 to about 70 weight percent, suitably from about 30 to about 65 weight percent, and more suitably from about 35 to about 60 weight percent wettable staple fiber, with all weight percents based on the total weight of the wettable staple fiber, hydrogel-forming polymeric material, and wettable binder fiber in the absorbent structure.

As used herein, the term "otherwise essentially identical absorbent structure without any wettable binder fiber" and other similar terms are intended to refer to a control absorbent structure that is prepared using essentially identical materials and an essentially identical process as compared to an absorbent structure of the present invention, except that the control absorbent structure does not comprise or is not prepared with the wettable binder fiber described herein but, instead, comprises an amount of additional wettable staple fiber essentially identical to the amount of wettable binder fiber used in the absorbent structure of the present invention. As such, the otherwise essentially identical absorbent structure without any wettable binder fiber and the absorbent structure of the present invention will generally have essentially identical basis weights. As a result of not comprising the wettable binder fiber, the otherwise essentially identical absorbent structure generally will not exhibit the desired absorbent properties described herein as compared to an absorbent structure of the present invention.

As used herein, the term "binder fiber" is meant to refer to a fiber that acts to form a composite web when the binder fiber is in its final form in the absorbent structure herein. As such, the binder fibers interact with each other in some manner to form a composite web. Such interaction of the binder fibers may be in the form of entanglement or an adhesive interaction whereby the binder fibers are treated as, for example, by heating the binder fibers above their softening point temperature and allowing the binder fibers to contact each other to form adhesive bonds. Once treated in such a manner, the binder fibers cannot be reclaimed in their original form. This is in contrast to the staple fibers and hydrogel-forming polymeric material which substantially retain their individual form, although such staple fibers and hydrogel-forming polymeric material may be adhered to by the binder fibers in the absorbent structures of the present invention.

The binder fiber may generally be formed from any thermoplastic composition capable of extrusion into fibers. Examples of such thermoplastic compositions include polyolefins such as polypropylene, polyethylene, polybutenes, polyisoprene, and their copolymers; polyesters such as polyethylene terephthalate; polyamides such as nylon; as well as copolymers and blends of these and other thermoplastic polymers.

A suitable binder fiber for the present invention comprises meltblown fibers formed from a hydrophilic polypropylene material. Such meltblown fibers are typically very fine fibers prepared by extruding liquefied, or melted, fiber-forming copolymer through orifices in a die into a high velocity gaseous stream. The fibers are attenuated by the gaseous stream and are subsequently solidified. The resulting stream of solidified binder fibers can be collected as, for example, on a screen disposed in the gaseous stream, as an entangled coherent fibrous mass. Such an entangled fibrous mass is characterized by extreme entanglement of the binder fibers. This entanglement provides coherency and strength to the resulting web structure. Such entanglement also adapts the web structure to constrain or entrap the staple fiber and the hydrogel-forming polymeric material within the structure after the staple fiber and the hydrogel-forming polymeric material have been incorporated into the web structure, either during or after formation of the web structure. The binder fibers are entangled sufficiently that it is generally impossible to remove one complete binder fiber from the mass of binder fibers or to trace one binder fiber from beginning to end.

As used herein, the constraining or entrapment of the staple fiber and the hydrogel-forming polymeric material within the web structure is meant to represent that the staple fiber and the hydrogel-forming polymeric material are substantially immobilized, such that the staple fiber and the hydrogel-forming polymeric material are not free to substantially move or migrate within or out of the web structure. Such constraining or entrapment may be, for example, by adhesive means or by the entanglement of the binder fibers of the web structure.

The binder fiber used herein may be circular but may also have other cross-sectional geometries such as elliptical, rectangular, triangular, or multi-lobal.

Suitably, in addition to, for example, the polypropylene component, a hydrophilic polypropylene material will also generally comprise a hydrophilizing polymeric component. Any polymeric component capable of being polymerized with the polypropylene component, and capable of hydrophilizing the resultant copolymeric material to render it wettable according to the definition of the present invention, is suitable for use in the present invention.

The fiber-forming hydrophilic polypropylene copolymer material may be either a block or a graft copolymer formed from its respective polypropylene and hydrophilizing polymeric components. Processes for preparing both block and graft copolymers, in general, are known in the art. Whether the copolymer useful for the fibers herein is a block or a graft copolymer will depend upon the particular nature of the hydrophilizing polymeric component which is utilized in forming the copolymer.

The wettable binder fibers should be present in the absorbent structure of the present invention in an amount effective to provide sufficient support or bulk to the absorbent structure, to effectively constrain or entrap the wettable staple fiber and hydrogel-forming polymeric material, and to result in the desired improvement in absorbent properties as compared to an otherwise essentially identical absorbent structure that does not comprise any wettable binder fiber.

As such, the wettable binder fiber should be present in the absorbent structure in more than a minimal amount so that the absorbent structure does not experience an undesirable loss of integrity or an undesirable structure collapse when the absorbent structure becomes saturated with a liquid. However, the wettable binder fiber should be present in the absorbent structure in less than an excessive amount so that the wettable binder fiber does not undesirably restrict the hydrogel-forming polymeric material from swelling or otherwise undesirably affect the absorbent properties of the absorbent structure as it becomes saturated with liquid.

The wettable binder fiber is therefore desirably present in an absorbent structure of the present invention in an amount of from greater than about 7 to about 40 weight percent, suitably from about 8 to about 35 weight percent, and more suitably from about 10 to about 30 weight percent wettable binder fiber, with all weight percents based on the total weight of the wettable staple fiber, hydrogel-forming polymeric material, and wettable binder fiber in the absorbent structure.

The absorbent structure of the present invention preferably comprises a fibrous matrix comprising the wettable binder fiber wherein the fibrous matrix constrains or entraps the wettable staple fiber and the hydrogel-forming polymeric material.

The fibrous matrix may be formed by air-laying fibers, through a spunbond or meltblown process, a carding process, a wet-laid process, or through essentially any other means, known to those skilled in the art, for forming a fibrous matrix.

Methods of incorporating the hydrogel-forming polymeric material and wettable staple fiber into the fibrous matrix are known to those skilled in the art. Suitable methods include incorporating the hydrogel-forming polymeric material and wettable staple fiber into the matrix during formation of the matrix, such as by air laying the fibers of the fibrous matrix and the hydrogel-forming polymeric material and/or wettable staple fiber at the same time or wet-laying the fibers of the fibrous matrix and the hydrogel-forming polymeric material and/or wettable staple fiber at the same time. Alternatively, it is possible to apply the hydrogel-forming polymeric material and/or wettable staple fiber to the fibrous matrix after formation of the fibrous matrix. Other methods include sandwiching the hydrogel-forming polymeric material between two sheets of material, at least one of which is fibrous and liquid permeable. The hydrogel-forming polymeric material may be generally uniformly located between the two sheets of material or may be located in discrete pockets formed by the two sheets. It is preferable that the wettable staple fiber be generally uniformly distributed within the fibrous matrix. However, the wettable staple fiber may be nonuniformly distributed as long as the desired improvement in Z-direction liquid permeability of the absorbent structure is still achieved.

The fibrous matrix may be in the form of a single, integrally formed layer or of a composite comprising multiple layers. If the fibrous matrix comprises multiple layers, the layers are preferably in liquid communication with one another, such that, a liquid present in one fibrous layer can flow or be transported to the other fibrous layer. For example, the fibrous layers may be separated by cellulosic tissue wrap sheets known to those skilled in the art.

The hydrogel-forming polymeric material may be distributed in the individual layers in a generally uniform manner or may be present in the fibrous layers as a layer or other nonuniform distribution.

When the fibrous matrix comprises a single, integrally formed layer, the concentration of hydrogel-forming polymeric material may increase along the thickness of the fibrous matrix in a gradual, nonstepwise fashion or in a more stepwise fashion. Similarly, the density may decrease through the thickness in a nonstepwise manner or in a stepwise manner.

The absorbent structures of the present invention may generally be of any size or dimension as long as the absorbent structure exhibits the desired absorbent characteristics as described herein. Typically, the absorbent structures will have a volume of at least about 18 cubic centimeters, such as with a width of about 6 centimeters, a length of about 6 centimeters, and a depth of about 0.5 centimeter. Suitably, the absorbent structure will have a volume of at least about 60 cubic centimeters, such as with a width of about 10 centimeters, a length of about 6 centimeters, and a depth of about 1 centimeter.

The absorbent structure of the present invention may also be used or combined with other absorbent structures, with the absorbent structure of the present invention being used as a separate layer or as an individual zone or area within a larger, composite absorbent structure. The absorbent structure of the present invention may be combined with other absorbent structures by methods well known to those skilled in the art, such as by using adhesives or simply by layering the different structures together and holding together the composite structures with, for example, a tissue sheet.

The absorbent structures according to the present invention are suited to absorb many liquids, such as water, saline, and synthetic urine, and body liquids such as urine, menses, and blood, and are suited for use in disposable absorbent products such as diapers, adult incontinent products, and bed pads; in catamenial devices such as sanitary napkins and tampons; and in other disposable absorbent products such as wipes, bibs, wound dressings, and surgical capes or drapes. Accordingly, in another aspect, the present invention relates to a disposable absorbent product comprising an absorbent structure as described herein.

Use of the described absorbent structures in disposable absorbent products allows for the formation of a disposable absorbent product which is able to rapidly receive a discharged liquid and, yet, which disposable absorbent product is thin.

In one embodiment of the present invention, a disposable absorbent product is provided, which disposable absorbent product comprises a liquid-permeable topsheet, a backsheet attached to the topsheet, and an absorbent structure positioned between the topsheet and the backsheet.

While one embodiment of the invention will be described in terms of the use of an absorbent structure in an infant diaper, it is to be understood that the absorbent structure is equally suited for use in other disposable absorbent products known to those skilled in the art.

Turning now to the drawing, FIG. 1 illustrates a disposable diaper 11 according to one embodiment of the present invention. Disposable diaper 11 includes a backsheet 12, a topsheet 14, and an absorbent structure 16, located between the backsheet 12 and the topsheet 14. Absorbent structure 16 is an absorbent structure according to the present invention.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films. Absorbent products and structures according to all aspects of the present invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

Absorbent structures comprising fibers generally have pores or capillaries between the fibers that are used to acquire, distribute, and store a liquid that is contacted with the absorbent structure.

However, many staple fibers, such as wood pulp fibers, are not very stiff and do not have very good resiliency or integrity when wetted with a liquid. Absorbent structures that comprise fibers that consist essentially of staple fibers, such as wood pulp fibers, have been found, upon sufficient saturation with a liquid, to generally become highly flexible and to collapse to a less thick, higher density structure. Such a collapse of the absorbent structure generally results in a decrease of the average pore size between the staple fibers as well as a decrease in the total pore volume of the absorbent structure. Such decreases generally result in the absorbent structure leaking the liquid with which the absorbent has been contacted, since the absorbent structure generally has a reduced capacity for the liquid. The absorbent structure generally also has a reduced ability to imbibe the liquid as quickly as the liquid is contacted with the absorbent structure. In addition, the absorbent structure generally has a reduced ability to transfer or distribute the liquid within the absorbent structure.

Furthermore, such an absorbent structure that comprises fibers that consist essentially of staple fibers, such as wood pulp fibers, generally loses its integrity when wetted with a liquid. Such a loss of integrity in the absorbent structure generally results in the absorbent structure breaking apart and being difficult to handle without the use of enclosing materials such as a tissue wrap sheet.

The present invention addresses these problems by adding an amount of binder fiber to the absorbent structure. The addition of the binder fiber to the absorbent structure has been found to impart integrity to the absorbent structure both when the absorbent structure is in a dry condition and when the absorbent is in a 100 percent liquid saturated condition. This enables much easier handling of the absorbent structure and helps to prevent the absorbent structure from breaking apart during handling and during use, particularly when the absorbent structure is wet. The integrity of a material can be quantified by the tensile strength of the material, representing the cohesive strength of the material. As such, the tensile strength of a material represents the maximum load that may be placed on the material before the material breaks apart, or in other words, cohesively fails. A tensile strength that is too low will generally mean that a material will not have very good integrity and will easily break apart, particularly when saturated with liquid.

As will be appreciated by one skilled in the art, a material such as an absorbent structure may entrap a relatively minor amount of liquid, such as water, within the material prior to use. For example, such liquid may be absorbed by the absorbent structure from humidity in the air. Such an absorbent structure is still intended to be considered in a dry condition for purposes of the present invention. Thus, as used herein, the "dry condition" of a material is meant to represent that the material comprises an amount of liquid that is suitably less than about 5 weight percent, more suitably less than about 3 weight percent, and most suitably less than about 1 weight percent, based on the total weight of the material.

As used herein, the "100 percent liquid saturated condition" of a material is meant to represent that the material comprises an amount of liquid that is about 100 percent of the absolute liquid saturated retention capacity of the material.

It is desired that the absorbent structure of the present invention exhibits a Tensile Strength value in a dry condition that is at least about 50 percent greater, suitably at least about 100 percent greater, more suitably at least about 250 percent greater, and most suitably at least about 400 percent greater, than the Tensile Strength value exhibited by an otherwise essentially identical absorbent structure without any wettable binder fiber in a dry condition.

It is also desired that the absorbent structure of the present invention exhibits a Tensile Strength value in a dry condition that is at least about 400 grams force, suitably at least about 500 grams force, more suitably at least about 750 grams force, and most suitably at least about 1000 grams force.

It is desired that the absorbent structure of the present invention exhibits a Tensile Strength value in a 100 percent liquid saturated condition that is at least about 50 percent greater, suitably at least about 100 percent greater, more suitably at least about 250 percent greater, and most suitably at least about 400 percent greater, than the Tensile Strength value exhibited by an otherwise essentially identical absorbent structure without any wettable binder fiber in a 100 percent liquid saturated condition.

It is also desired that the absorbent structure of the present invention exhibits a Tensile Strength value in a 100 percent liquid saturated condition that is at least about 400 grams force, suitably at least about 500 grams force, more suitably at least about 750 grams force, and most suitably at least about 1000 grams force.

The addition of the binder fiber to the absorbent structure has also been found to assist in preventing a collapse of the capillary or pore structure of the absorbent structure when the absorbent structure is wet. This helps to substantially maintain the pore volume of the absorbent structure as the absorbent structure becomes saturated with liquid. The necessity to maintain the pore volume of the absorbent structure becomes even more critical in relatively thin disposable absorbent structures, such as diapers, where the absorbent structure has a relatively small pore volume to begin with and any pore volume increase resulting from the swelling of any hydrogel-forming polymeric material with liquid should not be lost due to the collapse of the staple fibers. The resistance to collapse of the capillary or pore structure of the absorbent structure may be quantified by the compression resistance of the absorbent structure. As used herein, the compression resistance of a material is meant to represent the inverse of the change in thickness, in millimeters, of the material when subjected to a pressure. The Compression Resistance value of a material may be measured according to the Test Methods section herein.

In particular, it is desired that the absorbent structure of the present invention exhibits a Compression Resistance value that is at least about 25 percent greater, suitably at least about 30 percent greater, more suitably at least about 50 percent greater, and most suitably at least about 100 percent greater, than the Compression Resistance value exhibited by an otherwise essentially identical absorbent structure without any wettable binder fiber, wherein the Compression Resistance value represents the inverse of the change in thickness of an absorbent structure when subjected to a pressure of about 0.5 pounds per square inch as compared to the thickness of the absorbent structure when not subjected to the pressure.

It is also desired that the absorbent structure of the present invention exhibits a Compression Resistance value that is at least about 0.15/millimeter, suitably at least about 0.17/millimeter, more suitably at least about 0.19/millimeter, and most suitably at least about 0.25/millimeter.

The resistance to collapse by the absorbent structure of the present invention when wet also been found to assist in improving the z-direction permeability of the absorbent structure as the absorbent structure becomes saturated with liquid. In general, the absorbent structures of the present invention have been found to exhibit improved z-direction permeability upon liquid saturation as compared to an otherwise essentially identical absorbent structure not comprising a wettable binder fiber. As used herein, the "z-direction permeability" of an material is meant to represent the resistance by the material to liquid flow through the depth of the material. In general, the higher the z-direction permeability value of a material, the smaller the resistance of the material to liquid flow in the z-direction of or, in other words, through the thickness of the material. Likewise, the lower the z-direction permeability value of a material, the greater the resistance of the material to liquid flow in the z-direction of the material.

In particular, the absorbent structures of the present invention have been found to exhibit a Z-Direction Permeability value at 60 percent saturation that is not less than, suitably at least about 20 percent greater than, more suitably at least about 25 percent greater than, and most suitably at least about 30 percent greater than, the Z-Direction Permeability value of the absorbent structure at 30 percent saturation. This is in contrast to an otherwise essentially identical absorbent structure without any wettable binder fiber which generally exhibits a Z-Direction Permeability value at 60 percent saturation that is much less than the Z-Direction Permeability value at 30 percent saturation.

The absorbent structure of the present invention desirably has a Z-Direction Permeability value at 60 percent saturation that is at least about 50 Darcy, beneficially at least about 75 Darcy, suitably at least about 100 Darcy, more suitably at least about 150 Darcy, and most suitably at least about 200 Darcy. The Darcy is a unit representing the permeability of a porous material and is equivalent to about $9.87 \times 10^{-9}$ square centimeters.

The absorbent structure of the present invention desirably has a Z-Direction Permeability value in a dry condition that is at least about 15 Darcy, suitably at least about 20 Darcy, more suitably at least about 25 Darcy, and most suitably at least about 30 Darcy.

As used herein, the "absolute liquid saturated retention capacity" of an absorbent structure is meant to represent the maximum amount of liquid the absorbent structure can retain when given a sufficient amount of time to reach 100 percent saturation and when an externally applied pressure of about 0.5 psi is applied to the saturated structure. Thus, as used herein, "60 percent saturation", "30 percent saturation", and other related terms are meant to represent that a material has been saturated with a specific amount of liquid based on the absolute liquid saturated retention capacity of the material.

The absorbent structures of the present invention suitably have a specific liquid saturated retention capacity on a gram of liquid absorbed to a gram of absorbent structure basis of about 8 g/g to about 40 g/g, beneficially of about 10 g/g to about 35 g/g, and more beneficially of about 15 g/g to about 30 g/g.

The absorbent structures of the present invention suitably have a basis weight of about 100 grams per square meter (g/sm) to about 1000 g/sm, beneficially of about 200 g/sm to about 800 g/sm, and more beneficially of about 300 g/sm to about 700 g/sm.

The absorbent structures of the present invention suitably have a density of about 0.03 gram per cubic centimeter (g/cc) to about 0.5 g/cc, beneficially of about 0.05 g/cc to about 0.45 g/cc, and more beneficially of about 0.08 g/cc to about 0.4 g/cc.

TEST METHODS

Liquid Saturated Retention Capacity

The liquid saturated retention capacity is determined as follows. The material to be tested, having a moisture content of less than about 7 weight percent, is weighed and submerged in an excess quantity of a 0.9 weight percent aqueous saline solution at room temperature (about 23° C.). The material to be tested is allowed to remain submerged for about 20 minutes. After the 20 minute submerging, the material 31 is removed and, referring to FIG. 5, placed on a TEFLON™ coated fiberglass screen 34 having 0.25 inch (0.6 cm) openings (commercially available from Taconic Plastics Inc., Petersburg, N.Y.) which, in turn, is placed on a vacuum box 30 and covered with a flexible rubber dam material 32. A vacuum of about 0.5 pound per square inch (about 3.5 kilopascals) is drawn on the vacuum box for a period of about 5 minutes with the use of, for example, a vacuum gauge 36 and a vacuum pump (38). The material being tested is then removed from the screen and weighed. The amount of liquid retained by the material being tested is determined by subtracting the dry weight of the material from the wet weight of the material (after application of the vacuum), and is reported as the absolute liquid saturated retention capacity in grams of liquid retained. If desired, the weight of liquid retained may be converted to liquid volume by using the density of the test liquid, and is reported as the liquid saturated retention capacity in milliliters of liquid retained. For relative comparisons, this absolute liquid saturated retention capacity value can be divided by the weight of the material 31 to give the specific liquid saturated retention capacity in grams of liquid retained per gram of tested material. If material, such as hydrogel-forming polymeric material or fiber, is drawn through the fiberglass screen while on the vacuum box, a screen having smaller openings should be used. Alternatively, a piece of tea bag or similar material can be placed between the material and the screen and the final value adjusted for the liquid retained by the tea bag or similar material.

Compression Resistance

A rectangular sample about 4 inches wide, about 6 inches long, about 0.17 inch thick, and with a basis weight of about 700 grams per square meter, is taken and weighed. It is placed in a bath of 0.9 weight percent aqueous saline solution and allowed to remain for 20 minutes. At the end of this time the sample is essentially fully saturated. The sample's thickness is measured using a bulk meter available, for example, from Mitutoyo, Japan (Model Number ID-1050ME). The sample is then placed on a vacuum box and covered with a rubber dam in a procedure similar to the liquid saturated retention capacity test method. A vacuum is applied corresponding to a pressure of 0.5 pounds per square inch (psi) for 5 minutes. The sample is then removed and the thickness of the sample is measured with the same bulk meter. Compression resistance, defined as the force on the sample divided by the work done on the sample, is equal to the inverse of change in thickness (in millimeters) of the sample at the given pressure. So at a pressure of 0.5 psi:

Compression Resistance=1/(thickness at 0 psi—thickness at 0.5 psi).

Tensile Strength

The tensile strength of a material is evaluated by using tensile tester, such as a Model 4201 Instron with Microcon II from the Instron Corporation, Canton Me. The machine is calibrated by placing a 100 gram weight in the center of the upper jaw, perpendicular to the jaw and hanging unobstructed. The tension cell used is a 5 kilogram electrically-calibrating self-identifying load cell. The weight is then displayed on the Microcon display window. The procedure is performed in a room with standard-condition atmosphere such as about a temperature of about 23° C. and a relative humidity of about 50 percent.

A rectangular sample about 2 inches by about 6 inches is weighed and pressure is applied to the sample to reach a desired density. The dry sample is then placed in the pneumatic action grips (jaws) with 1 inch by 3 inch rubber coated grip faces. The gauge length is about 4 inches and the crosshead speed is about 250 mm/minute. The crosshead speed is the rate at which the upper jaw moves upward pulling the sample until failure. The Tensile Strength value is the maximum load at failure, recorded in grams of force needed to compromise or tear the sample. The tensile strength is evaluated for the material in both a dry condition and a 100 percent liquid saturated condition. The tensile strength for the material in a 100 percent liquid saturated condition is done by placing a dry sample in the jaws of the tester and then wetting the sample with a desired amount of 0.9% saline solution, as determined by the absolute liquid saturated retention capacity of the material. A time of 10 minutes is allowed for the sample to equilibrate. Then the test is repeated as above for the sample in the dry state.

Tensile Strength=highest load at failure (in grams force)

Z-Direction Permeability

A round sample of about 3 inch diameter is first cut using a die cutter. The density of the sample is calculated by determining its weight and thickness. The apparatus consists of an upper cylinder and a lower cylinder. The lower cylinder has a piston that is filled with mineral oil close to the brim (about 1 cm below the top edge). The bottom of the piston in the lower cylinder is connected to a pressure transducer, such as a Shaevitz Model No. P3061-50. The piston is connected to a precision turned screw connected to a speed controlled motor, such as a Velmex Unislide (Model No. 4036W1J) that moves the piston up or down at a required speed (about 2 centimeters/minute). The pressure transducer is connected to a computer that records the pressure from the transducer as pascals/volts. A typical experiment consists of placing the sample on a wire screen on top of the lower cylinder. The top hollow cylinder is then screwed onto the lower cylinder to hold the sample in place during the experiment. First the mineral oil in the piston of the lower cylinder is moved up through the sample at a rate of about 2 centimeters/minute for about two minutes until all the air in the sample is displaced and the sample is saturated with mineral oil. Once saturated, the system is allowed to come to equilibrium by a measured pause time of about 20 seconds. The pressure recorded by the computer at this time is the base line pressure. Then the mineral oil is moved up again through the sample at about 2 centimeters/minute and the maximum pressure is recorded by the computer. The difference between the base line pressure and the maximum pressure is delta P, (in dynes per square centimeter). The sample is then taken out. The viscosity of mineral oil is known to be about 6 centipoise at about 23° C. Then using Darcy's formula, permeability 'K' is calculated as follows:

K=(viscosity)×(speed)×(thickness of sample/delta P)

Where viscosity is the viscosity of the liquid (in centipoise), speed is the speed of the mineral oil (in centimeters per second), and thickness is the thickness of the sample (in centimeters).

K is referred to used herein as the Z-Direction Permeability value. This would be the Z-Direction Permeability value for a sample at about 0 percent saline saturation. The experiment is repeated for samples at about 30 percent and about 60 percent saturation by taking a similar but new sample each time and adding enough 0.9% saline solution to give a 30 percent or 60 percent saturation of the material. The amount of saline needed is calculated from the liquid saturated retention capacity of the sample.

EXAMPLE

Absorbent structures were prepared comprising a hydrogel-forming polymeric material, a wettable staple fiber and a wettable binder fiber. For the hydrogel-forming polymeric material, a partial sodium salt of a crosslinked polypropenoic acid high-absorbency material, available from The Dow Chemical Company under the designation Sharpei AFA 65-34, was used. For the wettable staple fiber, cellulosic wood pulp fluff was used. For the wettable binder fiber, a polypropylene homopolymer comprising less than about 2 weight percent of stabilizers, available from Himont U.S.A., Inc. under the trade name designation Valtec polypropylene homopolymer spheres, grade PF-015, combined with about 2 weight percent of an internal wetting agent, available from PPG Industries Inc., under the designation SF-19, was used. The wetting agent was compounded with the polypropylene before being extruded into a fiber with an average diameter of about 5 microns.

The wettable binder fiber was meltblown into an entangled composite web with the hydrogel-forming polymeric material fed into the meltblown stream and the staple fiber fed into the composite web structure with a picker roll.

Sample 4 was a control sample that does not include any wettable binder fiber. Sample 4 was prepared by an airforming process where the wettable staple fibers and the hydrogel-forming polymeric material were mixed by an air stream and then airlaid into a web on top of a vacuum box. The composite web formed was then wrapped with a light basis weight tissue paper to allow for handling and testing of the sample.

The absolute and relative basis weight amounts used of the different materials for various samples is indicated in Table 1. The basis weight amounts are given in grams per square meter (g/sm) of absorbent structure formed. The initial dry density of each sample material was about 0.17 grams per cubic centimeter.

The samples were evaluated for liquid saturated retention capacity, compression resistance, tensile strength, and z-direction permeability according to the procedures described herein. The results are described in Table 2.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

TABLE 1

| Sample No. | Binder Fiber Basis Weight | | Hydrogel Basis Weight | | Staple Fiber Basis Weight | | Total Bias |
|---|---|---|---|---|---|---|---|
| | (g/sm) | % | (g/sm) | % | (g/sm) | % | (g/sm) |
| 1 | 51 | 7 | 253 | 35 | 419 | 58 | 722 |
| 2 | 72 | 10 | 253 | 35 | 397 | 55 | 722 |
| 3 | 183 | 25 | 255 | 35 | 292 | 40 | 729 |
| 4* | 0 | 0 | 245 | 35 | 455 | 65 | 700 |

*Not an example of the present invention.

TABLE 2

| Sample No. | Compression Resistance (1/mm) | Tensile Strength (grams force) | | Absolute Liquid Saturated Retention Capacity (ml) | Z-Direction Permeability (Darcy) Saturation | | |
|---|---|---|---|---|---|---|---|
| | | Dry | Saturated | | 0% | 30% | 60% |
| 1 | 0.19 | 436 | 488 | 130 | 57.3 | 153.6 | 69.6 |
| 2 | 0.28 | 1314 | 1292 | 124 | 45.7 | 166.3 | 221.7 |
| 3 | 0.17 | 4570 | 3938 | 127 | 32.7 | 190.6 | 256.8 |
| 4* | 0.13 | 220 | 144 | 90 | 29.1 | 122.1 | 77.1 |

*Not an example of the present invention.

What is claimed is:

1. An absorbent structure comprising:
   a. from about 20 to about 65 weight percent hydrogel-forming polymeric material;
   b. from about 25 to about 70 weight percent wettable staple fiber; and
   c. from greater than about 7 to about 40 weight percent wettable binder fiber; wherein all weight percents are based on the total weight of the hydrogel-forming polymeric material, wettable staple fiber, and wettable binder fiber in the absorbent structure, wherein the absorbent structure exhibits a Z-Direction Permeability value at about 60 percent saturation that is greater than about 50 Darcy and that is not less than the Z-Direction Permeability value of the absorbent structure at about 30 percent saturation, wherein the Z-Direction Permeability values are determined according to the procedure described in the Test Methods section of the specification.

2. The absorbent structure of claim 1 comprising from about 25 to about 60 weight percent of the hydrogel-forming polymeric material.

3. The absorbent structure of claim 1 wherein the hydrogel-forming polymeric material is a polyacrylate material.

4. The absorbent structure of claim 1 comprising from about 30 to about 65 weight percent of the wettable staple fiber.

5. The absorbent structure of claim 1 wherein the wettable staple fiber has a fiber length from about 0.1 to about 15 centimeters.

6. The absorbent structure of claim 1 wherein the wettable staple fiber is selected from the group consisting of cellulosic fibers, textile fibers, and synthetic polymeric fibers.

7. The absorbent structure of claim 1 wherein the wettable staple fiber is wood pulp fiber.

8. The absorbent structure of claim 1 comprising from about 8 to about 35 weight percent wettable binder fiber.

9. The absorbent structure of claim 8 comprising from about 10 to about 30 weight percent of the wettable binder fiber.

10. The absorbent structure of claim 1 wherein the wettable binder fiber is a meltblown fiber comprising a polyolefin.

11. The absorbent structure of claim 1 wherein the absorbent structure comprises a fibrous matrix comprising the wettable binder fiber, wherein the fibrous matrix constrains the wettable staple fiber and the hydrogel forming polymeric material.

12. The absorbent structure of claim 1 wherein the absorbent structure exhibits a Z-Direction Permeability value at about 60 percent saturation that is at least about 20 percent greater than the Z-Direction Permeability value of the absorbent structure at about 30 percent saturation.

13. The absorbent structure of claim 12 wherein the Z-Direction Permeability value of the absorbent structure at about 60 percent saturation is at least about 25 percent greater than the Z-Direction Permeability value of the absorbent structure at about 30 percent saturation.

14. The absorbent structure of claim 1 wherein the absorbent structure exhibits a Z-Direction Permeability value at about 60 percent saturation that is greater than about 75 Darcy.

15. The absorbent structure of claim 14 wherein the Z-Direction Permeability value of the absorbent structure at about 60 percent saturation that is greater than about 100 Darcy.

16. The absorbent structure of claim 1 wherein the absorbent structure exhibits a Compression Resistance value that is at least about 25 percent greater than the Compression Resistance value exhibited by an otherwise essentially identical absorbent structure without any wettable binder fiber.

17. The absorbent structure of claim 1 wherein the absorbent structure exhibits a Compression Resistance value that is at least about 0.15/millimeter.

18. The absorbent structure of claim 1 wherein the absorbent structure exhibits a Tensile Strength value in a dry condition that is at least about 50 percent greater than the Tensile Strength value exhibited by an otherwise essentially identical absorbent structure without any wettable binder fiber in a dry condition, and wherein the absorbent structure exhibits a Tensile Strength value in a 100 percent liquid saturated condition that is at least about 50 percent greater than the Tensile Strength value exhibited by an otherwise essentially identical absorbent structure without any of the wettable binder fiber in a 100 percent liquid saturated condition.

19. The absorbent structure of claim 1 wherein the absorbent structure exhibits a Tensile Strength value in a dry condition that is at least about 400 grams force, and wherein the absorbent structure exhibits a Tensile Strength value in a 100 percent liquid saturated condition that is at least about 400 grams force.

20. An absorbent structure comprising:
   a. from about 25 to about 60 weight percent hydrogel-forming polymeric material;
   b. from about 30 to about 65 weight percent wettable wood pulp fiber; and
   c. from about 8 to about 35 weight percent wettable meltblown fiber comprising a polyolefin; wherein all weight percents are based on the total weight of the hydrogel forming polymeric material, wettable wood pulp fiber, and wettable meltblown fiber comprising a polyolefin in the absorbent structure, wherein the absorbent structure exhibits a Z-Direction Permeability value at about 60 percent saturation that is greater than about 75 Darcy and that is about 20 percent greater than the Z-Direction Permeability value of the absorbent structure at about 30 percent saturation, wherein the absorbent structure exhibits a Tensile Strength value in a dry condition that is at least about 50 percent greater than the Tensile Strength value exhibited by an otherwise essentially identical absorbent structure without any wettable binder fiber in a dry condition, and wherein the absorbent structure exhibits a Tensile Strength value in a 100 percent liquid saturated condition that is at least about 50 percent greater than the Tensile Strength value exhibited by an otherwise essentially identical absorbent structure without any of the wettable binder fiber in a 100 percent liquid saturated condition, wherein the Z-Direction Permeability values are determined according to the procedure described in the Test Methods section of the specification.

21. A disposable absorbent product comprising:
   a liquid-permeable topsheet, a backsheet, and an absorbent structure positioned between the topsheet and the backsheet, wherein the absorbent structure comprises:
   a. from about 20 to about 65 weight percent hydrogel-forming polymeric material;
   b. from about 25 to about 70 weight percent wettable staple fiber; and
   c. from greater than about 7 to about 40 weight percent wettable binder fiber;
wherein all weight percents are based on the total weight of the hydrogel-forming polymeric material, wettable staple fiber, and wettable binder fiber in the absorbent structure, wherein the absorbent structure exhibits a Z-Direction Permeability value at about 60 percent saturation that is greater than about 50 Darcy and that is not less than the Z-Direction Permeability value of the absorbent structure at about 30 percent saturation, wherein the Z-Direction Permeability values are determined according to the procedure described in the Test Methods section of the specification.

* * * * *